United States Patent

Nishino et al.

Patent Number: 6,083,987
Date of Patent: Jul. 4, 2000

[54] PHENYLENEDIAMINE DERIVATIVE, RADICAL SCAVENGER, BRAIN-INFARCTION DEPRESSANT, AND BRAIN-EDEMA DEPRESSANT

[75] Inventors: Chikao Nishino; Kazuyuki Miyazawa, both of Kanagawa; Hideo Kanno, Tokyo, all of Japan

[73] Assignee: Shiseido Co., Ltd., Tokyo, Japan

[21] Appl. No.: 09/089,236

[22] Filed: Jun. 2, 1998

[51] Int. Cl.[7] .................. A61K 31/166; A61K 31/18; C07C 307/00; C07C 235/42

[52] U.S. Cl. .................. 514/599; 514/602; 514/613; 514/617; 514/622; 564/88; 564/90; 564/92; 564/169; 564/171; 564/175; 564/176; 564/182; 564/183

[58] Field of Search .................. 564/169, 171, 564/175, 176, 182, 183, 88, 90, 92; 514/599, 602, 613, 617, 622

[56] References Cited

FOREIGN PATENT DOCUMENTS

| 3830054 A1 | 3/1990 | Germany | 560/49 |
|---|---|---|---|
| 6-116143 | 4/1994 | Japan . | |
| 9067327 | 3/1997 | Japan | 564/171 |

OTHER PUBLICATIONS

Klosa, J. Praket. Chem. 19(4), 45–55(1963) (With Chemical Abstract 11349), German language, 1963.

Gupta,, Gupta, Search for New Local Anaesthetics. Part IV, English Language, J. Indian Chem. Soc. 34.528–530(1957).

Hassner et al., , Synthetic Methods. Part 23 Rearrangement of Some Hydroxamic Acids Into Amides. A Self–Condensation Leading to Disproportionation English Language, J. Chem. Soc. Perkin. Trans. 733–737(1988).

Shiseido Co., Ltd., Abstract, Jap. Patent Application 07344947, Jun. 17, 1997.

*Primary Examiner*—Alan L. Rotman
*Attorney, Agent, or Firm*—Snider & Associates; Ronald R. Snider

[57] ABSTRACT

A phenylenediamine derivative or a salt thereof in accordance with the present invention is expressed by the following formula 1:

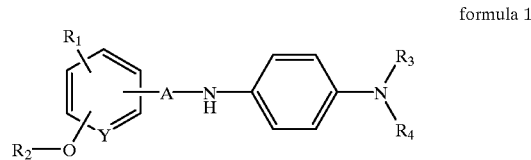

formula 1 wherein A represents a group expressed by $-CO-$, $-CH_2CO-$, $-CS-$, or $-SO_2-$; Y represents a carbon atom or nitrogen atom; $R_1$ represents a lower alkyl group; $R_2$ represents a hydrogen, lower alkyl, alkenyl, benzyl, or benzoyl group; and each of $R_3$ and $R_4$ represents an alkyl group having 1–10 carbon atoms. The phenylenediamine derivative above mentioned, as a radical scavenger, has antioxidant effect and lipid peroxidation inhibitory activity so as to be available for inhibiting brain infarction or brain edema.

18 Claims, 4 Drawing Sheets

Reaction formula A

Reaction formula B

Reaction formula C

Reaction formula D

Reaction formula E

Reaction formula F

Reaction formula G

Reaction formula H

Reaction formula I

Reaction formula J

Reaction formula K

PHENYLENEDIAMINE DERIVATIVE, RADICAL SCAVENGER, BRAIN-INFARCTION DEPRESSANT, AND BRAIN-EDEMA DEPRESSANT

RELATED APPLICATIONS

None.

FIELD OF THE INVENTION

The present invention relates to a phenylenediamine derivative and, in particular, to a derivative effective as a radical scavenger in organisms.

BACKGROUND OF THE INVENTION

In recent years, attention has been paid to influences of active oxygen and free radical upon organisms. Active oxygen and free radical are always generated and eliminated within an organism as long as the organism continues to live while using oxygen. In general, they act advantageously to the organism as a part of organism protection. However, when they are generated in an amount exceeding the protecting ability of the organism against the radical, they may attack the components of the organism constituting membranes and tissues of thereof, thereby causing various pathologies and malignancies. At present, the pathologies and diseases which may be attributable to active oxygen and free radical are numerous and their examples include cerebral nerves diseases such as brain infarction, brain edema, and parkinsonism; lung diseases such as lung oxygen intoxication and adult respiratory distress syndrome; circulation system diseases such as ischemic heart diseases (e.g., myocardial infarction and arrhythmia), and arteriosclerosis; and digestive organs diseases such as peptic ulcer, ulcerative colitis, and Crohn's disease.

Under these circumstances, consequently, there have been attempts to apply scavengers of active oxygen and free radical to medicaments for the above-mentioned diseases. For example, with respect to brain edema, mannitol, which is a mild radical scavenger, has been clinically used, though it is necessary continuous administration for two weeks. Recently, radical scavengers such as AVS (currently being applied) and MCI186 (currently being clinically tested in the third phase) have been developed recently. The sole target disease of these compounds is, however, brain edema. There has been no medical drug in which a radical scavenger is used for suppressing brain infarction.

On the other hand, a recombinant of SOD has become available and has been administered to patients so as to study its tissue-protecting effect. Acute myocardial infarction is one of its target diseases. By contrast, no radical scavenger other than SOD has been known as a medicament for this disease. With respect to arrhythmia, on the other hand, only lidocaine, which is a local anesthetic, has been clinically used.

SUMMARY OF THE INVENTION

In view of the foregoing prior art, an object of the present invention is to provide a low-molecular compound which is, as a radical scavenger, effective against brain edema and brain infarction.

Another object of the present invention is to provide a low-molecular compound which is effective against various diseases which are attributable to active oxygen and free radical.

As a result of diligent studies of the inventors for attaining the above mentioned objects, it has been found that a specific phenylenediamine derivative and its pharmacologically acceptable salts are effective, as a radical scavenger, against brain edema and brain infarction, thereby accomplishing the present invention.

Namely, a phenylenediamine derivative in accordance with the present invention is expressed by the following formula 1:

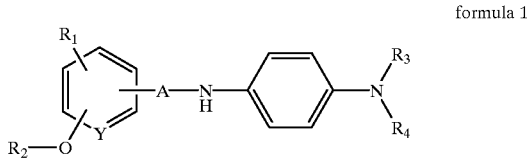

formula 1 wherein A represents a group expressed by —CO—, —$CH_2CO$—, —CS—, or —$SO_2$—; Y represents a carbon atom or nitrogen atom; $R_1$ represents a lower alkyl group; $R_2$ represents a hydrogen, lower alkyl, alkenyl, benzyl, or benzoyl group and each of $R_3$ and $R_4$ represents an alkyl group having 1 to 10 carbon atoms.

A radical scavenger in accordance with the present invention is characterized by comprising, as an effective ingredient, said phenylenediamine derivative or the pharmacologically acceptable salt thereof, together with a pharmaceutically acceptable carrier and/or adjuvant.

A brain infarction depressant in accordance with the present invention is characterized by comprising, as an effective ingredient, said phenylenediamine derivative or the pharmacologically acceptable salt thereof together with a pharmaceutically acceptable carrier and/or adjuvant.

A brain edema depressant in accordance with the present invention is characterized by comprising, as an effective ingredient, said phenylenediamine derivative or the pharmacologically acceptable salt thereof, together with a pharmaceutically acceptable carrier and/or adjuvant.

A method for inhibiting a brain infarction in man or manmals in accordance with the present invention is characterized by administering an effective amount of said phenylenediamine derivative or the pharmacologically acceptable salt thereof to a host.

A method for inhibiting a brain edema in man or manmals in accordance with the present invention is characterized by administering an effective amount of said phenylenediamine derivative or the pharmacologically acceptable salt thereof to a host.

DETAILED DESCRIPTION OF THE INVENTION

Figure 1:
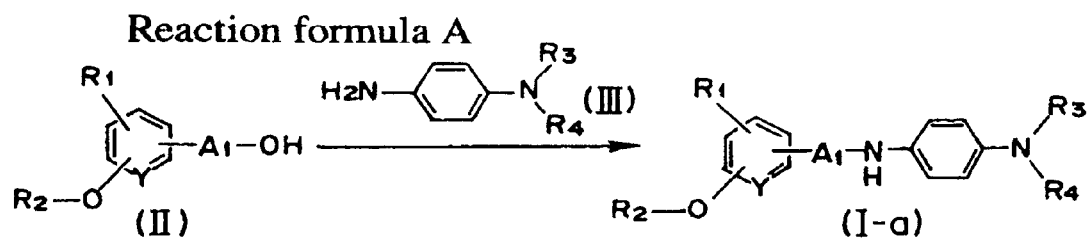
FIGS. 1 to 5 show examples of steps for manufacturing the phenylenediamine derivative in accordance with the present invention and FIGS. 6 to 11 show examples of steps for manufacturing material compounds for synthesizing the phenylenediamine derivative in accordance with the present invention.

In the above-mentioned formula 1 which represents a phenylenediamine derivative in accordance with the present invention, A represents a group expressed by —CO—, —$CH_2CO$—, —CS—, or —$SO_2$— and is preferably a group expressed by —CO—. Further, Y represent a carbon atom or nitrogen atom.

In each formula that represents a compound in accordance with the present invention, lower alkyl group found at $R_1$ refers to a straight or branched alkyl group having 1 to 6 carbon atoms. Examples thereof include methyl, ethyl, n-propyl, n-butyl, isopropyl, isobutyl, 1-methylpropyl, tert-butyl, n-pentyl, 1-ethylpropyl, isoamyl, and n-hexyl groups. Preferable example of the lower alkyl group is isobutyl groups.

$R_2$ represents a hydrogen atom, a lower alkyl, alkenyl, benzyl, or benzoyl group. Also, the definition of lower alkyl group in $R_2$ is the identical with the above-mentioned $R_1$. Alkenyl group found at $R_2$ refers to a straight or branched alkenyl group, which has 2 to 20 carbon atoms. It is preferably a branched alkenyl group and, more preferably, geranyl group. While the double bond has two kinds of configurations, namely, cis and trans, each double bond in alkenyl group may have either configuration.

When $R_2$ is benzyl or benzoyl group, it may be have a substituent $R_3$ and $R_4$ represent alkyl group having 1 to 10 carbon atoms and may be identical to or different from each other. In $R_3$ and $R_4$, alkyl group may be a straight or branched chain and is preferably methyl group.

The phenylenediamine derivative and its pharmacologically acceptable salts expressed by formula 1 that are preferable as a main ingredient of the radical scavenger, brain-infarction depressant, and brain-edema depressant in accordance with the present invention, as a radical scavenger, have antioxidant effect and lipid peroxidation suppressing effect as well as a high safety. Accordingly, they are effective as medicaments for preventing and curing various damages attributable to radicals generated by ischemic reperfusion or the like such as brain infarction and brain edema. Also, they are expected to be effective against the other ischemic reperfusion damages. Further, unlike the conventional radical scavengers, some kinds of the compound of the present invention has effective, by one drug, against both brain edema and brain infarction.

As similar compounds of a phenylenediamine derivative in accordance with the present invention, there have been known a phenylenediamine derivative having anti-thrombocyte aggregation effect in DE 3,830,054, a phenylenediamine derivative having anti-hypnotic effect anti-tumor effect and sedative effect in U.S. Pat. No. 2,870,146, a phenylenediamine derivative in J. Prakt. Chem. 19(4), 45( 1963). And a phenylenediamine derivative having local anesthesia effect in J. Indian. Chem. Soc. 34, 528(1957). However, these phenylenediamine derivatives have no relation to pharmacological effect of the present invention. Further, the derivative of the resent invention is characterized in that has a substituent expressed as $R_1$ and $R_2$—O— on benzene ring as shown in the above-mentioned formula 1. Such compound was not shown in the above. Thus, the phenylenedi amine of the present invention shown in the formula 1 is a novel compound.

A preferable example of a phenylenediamine derivative in accordance with the present invention is expressed by the following formula 2:

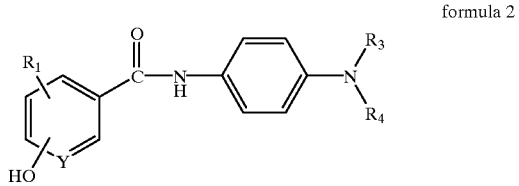

formula 2 wherein $R_1$, $R_3$, $R_4$, and Y are defined as those in formula 1.

Also, a preferable example of a phenylenediamine derivative in accordance with the resent invention is expressed by the following formula 3:

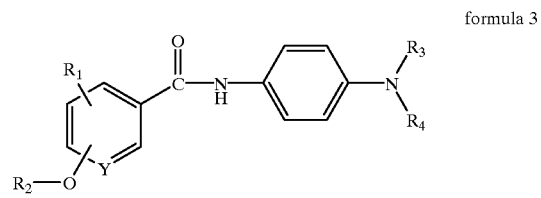

formula 3 wherein $R_2$ represents a lower alkyl, alkenyl, benzyl, or benzoyl group and $R_1$, $R_3$, $R_4$, and Y are defined as those in formula 1.

Further, a preferable example of a phenylenediamine derivative in accordance with the present invention is expressed by the following formula 4:

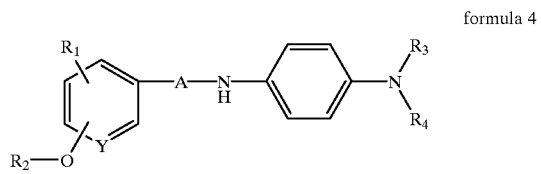

formula 4 wherein A represents a group expressed by —CH$_2$CO—, —CS—, or —SO$_2$— and $R_1$, $R_2$, $R_3$, and $R_4$ are defined as those in formula 1.

In formula 1–4, each of $R_3$ and $R_4$ is preferably methyl group and $R_1$ is preferably isobutyl group.

The compound (I), which is expressed by formula 1, can be made by reaction formulas A to E shown in FIGS. 1 to 5. As its manufacturing method, a general method disclosed in "New Experimental Chemistry Course" (Maruzen Co.) or "Peptide Synthesis" (Maruzen Co.), for example, can be used.

First, in reaction formula A shown in FIG. 1, $A_1$ represents —CO— or —CH$_2$CO—, while $R_1$, $R_2$, $R_3$, $R_4$ and Y are defined as those in formula (I).

In reaction formula A, from the carboxylic acid(II) and the amine(III), the amide(I-a) in accordance with the present invention can be obtained. In this reaction, known amide-bond forming reactions such as a method proceeding by way of a mixed anhydride, a method proceeding by way of an acid chloride, a method using a condensing agent, a method using a carbonyl diimidazole, and a method using with an azide can be used.

In the mixed anhydride method, an activator such as diphenylphosphinic chloride, phosphorus oxychloride, ethyl chloroformate, isobutyl chloroformate, or pivaloyl chloride is used to convert the carboxylic acid (II) into its corresponding acid anhydride and then the latter is reacted with the amine (III). As an additive, for example, an organic base such as triethylamine, pyridine, or N-methylmorpholine can be used. As a solvent, for example, a halogenated hydrocarbon such as dichloromethane or chloroform; an aromatic compound such as benzene, toluene, xylene, or pyridine; an ether such as tetrahydrofuran or dioxane; an amide such as dimethylformamide or dimethylacetamide; or dimethylsulfoxide can be used. While the reaction temperature and reaction time may be changed according to the material compounds used, the reaction is usually effected at a temperature within the range of −15° C. to the reflux temperature of the solvent.

In the acid chloride method, for example, phosphorus pentachloride, phosphorus trichloride, or thionyl chloride is used to convert the carboxylic acid (II) into its corresponding acid chloride and then the latter is reacted with the amine (III). As an additive, for example, an organic base such as triethylamine, pyridine, or N-methylmorpholine; an inorganic base such as sodium hydroxide; or a salt such as sodium acetate or potassium carbonate can be used. As a solvent, for example, a halogenated hydrocarbon such as dichloromethane or chloroform; an aromatic compound such as benzene, toluene, xylene, or pyridine; an ether such as diethyl ether, tetrahydrofuran, or dioxane; an amide such as dimethylformamide or dimethylacetamide; dimethylsulfoxide; water; or the mixture thereof can be used. While the reaction temperature and reaction time may be changed according to the material compounds used, the reaction is usually effected at a temperature within the range of 0° C. to the reflux temperature of the solvent.

In the method using a condensing agent, for example, a carbodiimide such as N, N'-dicyclohexylcarbodiimide (DCC) or 1-ethyl-(3-dimethylaminopropyl)carbodiimide hydrochloride (WSCI) or a chloride such as titanium tetrachloride or silicon tetrachloride can be used. As a solvent, for example, a halogenated hydrocarbon such as dichloromethane or chloroform; an aromatic compound such as benzene, toluene, xylene, or pyridine; an ether such as tetrahydrofuran or dioxane; an amide such as dimethylformamide or dimethylacetamide; or dimethylsulfoxide can be used. If necessary, this reaction may be effected while 1-hydroxy benzotriazole (HOBt) or N-hydroxysuccinimide (HOSu) is added thereto. While the reaction temperature and reaction time may be changed according to the material compounds used, the reaction is usually effected at a temperature within the range of −78° C. to the reflux temperature of the solvent.

In the method using carbonyl diimidazole (CDI), 1,1'-carbonyldiimidazole is used to convert the carboxylic acid (II) into its N-acyl derivative and then the latter is reacted with the amine (III). As a solvent, for example, a halogenated hydrocarbon such as dichloromethane or chloroform; an aromatic compound such as benzene, toluene, or xylene; an ether such as tetrahydrofuran or dioxane; an amide such as dimethylformamide or dimethylacetamide; or dimethylsulfoxide can be used. While the reaction temperature and reaction time may be changed according to the material compounds used, the reaction is usually effected at a temperature within the range of 0° C. to the reflux temperature of the solvent.

In the azide method, an activator such as diphenylphosphorylazide is used to convert the carboxylic acid (II) into its corresponding azide and then the latter is reacted with the amine (III). As an additive, for example, an organic base such as triethylamine, pyridine, or N-methylmorpholine can be used. As a solvent, for example, a halogenated hydrocarbon such as dichloromethane or chloroform; an aromatic compound such as benzene, toluene, xylene, or pyridine; an ether such as tetrahydrofuran or dioxane; an amide such as dimethylformamide or dimethylacetamide; or dimethylsulfoxide can be used. While the reaction temperature and reaction time may be changed according to the material compounds used, the reaction is usually effected at a temperature within the range of 0° C. to the reflux temperature of the solvent.

In the ester-bond formation by the dehydrating condensation, for example, methods using, as a catalyst, a mineral acid such as sulfuric acid or hydrochloric acid, an organic acid such as p-toluene sulfonic acid, or a Lewis acid such as boron trifluoride etherate or methods using a coexisting desiccating agent such as magnesium sulfate anhydride or molecular sieve can be used. Also, a condensing agent such as trifluoroacetic anhydride or N,N'-dicyclohexylcarbodiimide (DCC) can be used. In this case, pyridine, 4-dimethylaminopyridine, or the like can be used therewith. Further, in the presence of triphenylphosphine, diethyl diazocarboxylate can be used. As a solvent, for example, a halogenated hydrocarbon such as dichloromethane or chloroform; an aromatic compound such as benzene, toluene, xylene, or pyridine; an ether such as tetrahydrofuran or dioxane; or an amide such as N,N-dimethylformamide or N,N-dimethylacetamide can be used. While the reaction temperature and reaction time can be changed according to the material compounds used, the reaction is usually effected at a temperature within the range of 0° C. to the reflux temperature of the solvent.

Specifically, for example, in the method using the condensing agent, the carboxylic acid (II) is dissolved in dichloromethane, N,N-dimethylformamide, or the like and, after a condensing agent such as DCC or WSCI is added thereto, in or without the presence of HOBt or HOSu as an additive, and the resulting mixture is stirred, the amine (III) is added thereto and the reaction is effected at a temperature within the range of 0° C. to room temperature, thereby attaining the aimed object.

In the mixed acid anhydride method, the reaction is effected at a temperature within the range of 0° C. to room temperature in the solvent such as chloroform by using diphenylphosphinic chloride as an activating agent and triethylamine as an additive, thereby attaining the aimed object.

Figure 2:
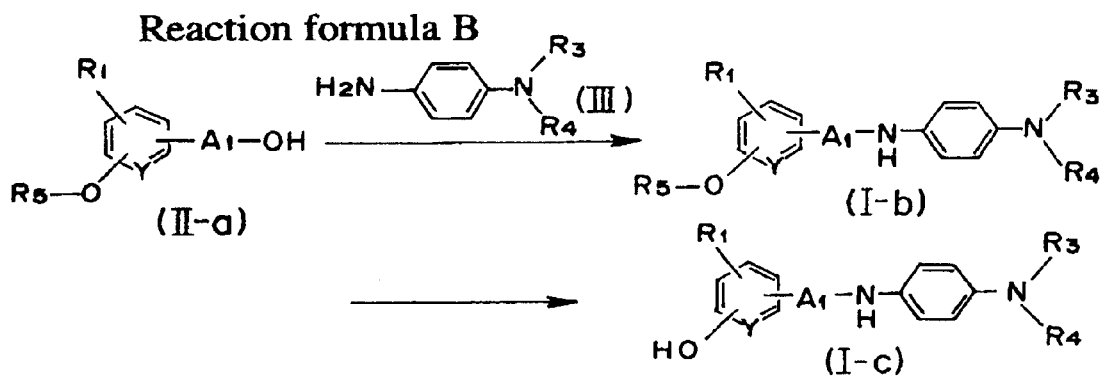

Also, the compound in accordance with the present invention can be obtained by reaction formula B shown in FIG. 2. In reaction formula B, $A_1$ represents —CO— or —CH$_2$CO—, while $R_1$, $R_3$, $R_4$, and Y are defined as those of formula (I). Also, $R_5$ represents a protective group of phenolic hydroxyl group and can use benzyl group, various substituted benzyl groups, benzyloxycarbonyl group, or tert-butyloxycarbonyl group, as long as no problem has occurred in the subsequent reaction.

In the first step of reaction formula B, the compound (I-b) can be obtained from carboxylic acid (II-a) and amine (III) by using condensation method described in formula A. In the second step of reaction formula B, the compound (I-c) can be obtained by putting the compound (I-b) into deprotection.

The deprotection can use various known methods according to the types of protective group $R_5$. For example, a reductive removal method or a method by treating with acid can be used in the case where $R_5$ is benzyl group.

Specifically, for example, palladium-carbon is used as catalyst under the catalytic reduction condition and the reaction is effected in the solvent such as ethanol and at a temperature within the range of room temperature to the reflux temperature of the solvent, thereby attaining the aimed object.

Figure 3:
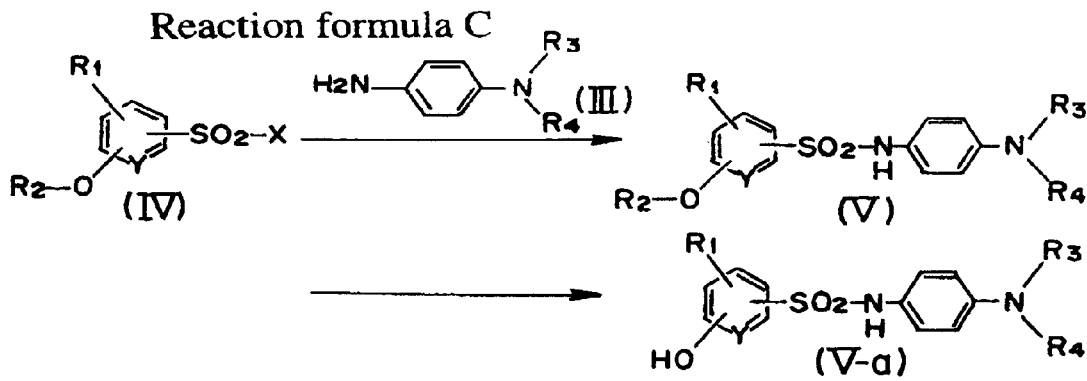

Also, the compound in accordance with the present invention can be obtained by reaction formula C shown in FIG. 3. In reaction formula C, $R_2$ represents a lower alkyl, alkenyl, benzyl, or benzoyl group, while $R_1$, $R_3$, $R_4$, and Y are defined as those of formula (I). Also, X represents a halogen atom.

In the first step of reaction formula C, sulfonyl amide compound (V) in accordance with the present invention can be obtained from sulfonyl halide (IV) and amine (III). In this reaction, for example, sodium hydroxide, potassium hydroxide, or organic base such as triethylamine, pyridine, or N-methylmorpholine can be used as an additive. As a solvent, for example, water; acetone; a halogenated hydrocarbon such as dichloromethane or chloroform; an aromatic compound such as benzene, toluene, xylene, or pyridine; an ether such as tetrahydrofuran or dioxane; or an amide such as dimethylformamide or dimethylacetamide can be used. While the reaction temperature and reaction time may be changed according to the material compounds used, the reaction is usually effected at a temperature within the range of $-15°$ C. to the reflux temperature of the solvent.

Specifically, for example, sulfonyl halide (IV) is dissolved in tetrahydrofuran, chloroform, or the like, amine (III) is added to the solution in the presence of triethylamine, sodium hydroxide, or the like. The reaction is effected at a temperature within the range of $-15°$ C. to the reflux temperature of the solvent, thereby attaining the aimed object.

In the second step of reaction formula C, the compound (V-a) can be obtained by deprotection of the compound (V). This deprotection can be conducted by the same condition with the second step in reaction formula B.

Figure 4:
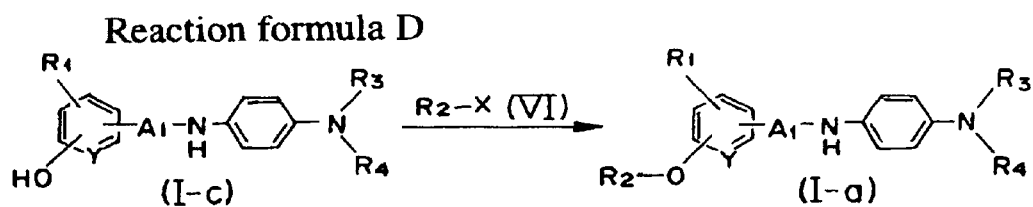

The compound in accordance with the present invention can be obtained by reaction formula D shown in FIG. 4. In reaction formula D, $A_1$ represents —CO— or —CH$_2$CO—, while X represents a halogen atom. $R_2$ represents a lower alkyl, alkenyl, benzyl, or benzoyl group, while $R_1$, $R_3$, $R_4$, Y, and n are defined as those of formula (I).

In reaction formula D, when a halide (VI) is reacted with the compound (I-c), the compound (I-a) of the present invention can be synthesized. This reaction can be effected in the presence of a base. Sodium amide, triethylamine, sodium hydride, sodium hydroxide, potassium carbonate, barium oxide, silver oxide, or the like can be used therefor. Also, a catalytic amount of potassium iodide can be added thereto. As a solvent, for example, an alcohol such as methanol, ethanol, or butanol; an aromatic compounds such as benzene, toluene, xylene, or pyridine; an ether such as diethylether, tetrahydrofuran, or dioxane; an amide such as N,N-dimethylformamide or N,N-dimethylacetamide; a sulfoxide such as dimethylsulfoxide; or a ketone such as acetone can be used. While the reaction temperature and reaction time may be changed according to the material compounds used, the reaction is usually effected at a temperature within the range of 0° C. to the reflux temperature of the solvent.

Specifically, for example, the compound (I-c) is dissolved in the solvent such as tetrahydrofuran, N,N-dimethylformamide, or the like and, after sodium hydride is added thereto and the resulting mixture is stirred, the halide (VI) is added thereto. The reaction is effected at a temperature within the range of room temperature to the reflux temperature of the solvent, thereby attaining the aimed object.

Figure 5:
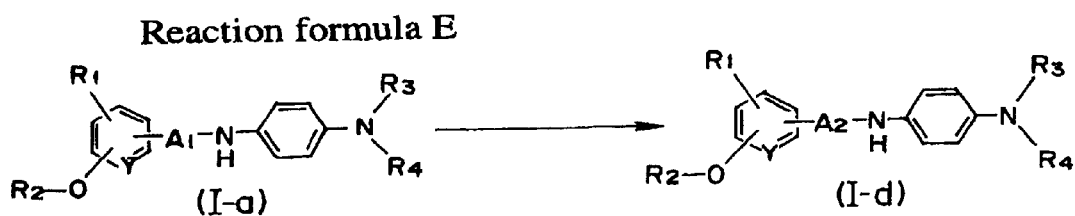
Figure 6:
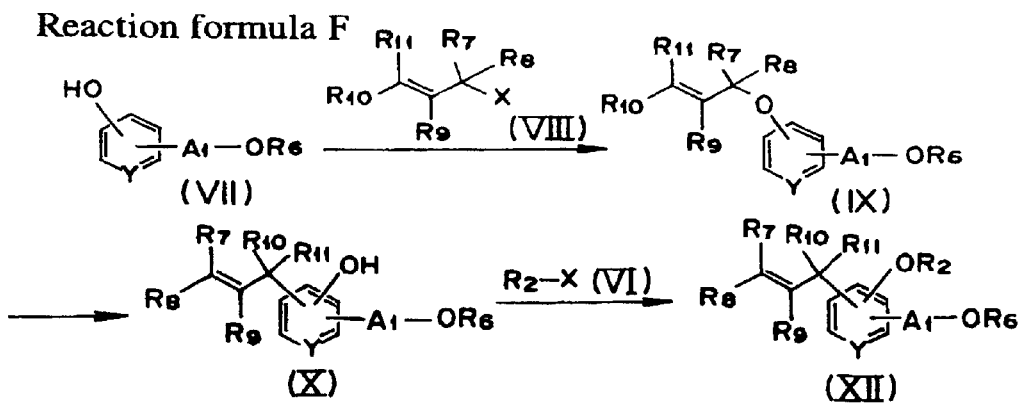

Also, the compound of the present invention can be obtained by reaction formula E shown in FIG. 5. In reaction formula E, $A_1$ represents —CO— or —CH$_2$CO—, while $A_2$ represents —CS— or —CH$_2$CS—. $R_1$, $R_2$, $R_3$, $R_4$, and Y are defined as those of formula (I).

In reaction formula E, the amide (I-a) is converted into the thioamide compound (I-d). Examples of the reagents used for this reaction include Lawesson's reagent (2,4-bis(4-methoxyphenyl)-1,3-dithia-2,4-diphosphetan-2,4-disulfide) and phosphorus pentasulfide. Also, imidoyl chloride obtained by the reaction of the amide compound (I-a) with phosgene can be reacted with hydrogen sulfide to synthesize the thioamide compound (I-d). As a solvent, for example, a halogenated hydrocarbon such as dichloromethane or chloroform; an aromatic compounds such as benzene, toluene, xylene, or pyridine; an ether such as tetrahydrofuran or dioxane; an amide such as N,N-dimethylformamide or N,N-dimethylacetamide; or dimethylsulfoxide can be used. While the reaction temperature and reaction time may be changed according to the material compounds used, the reaction is usually effected at a temperature within the range of 0° C. to the reflux temperature of the solvent.

Specifically, for example, the compound (I-a) is dissolved in the solvent such as toluene or the like, Lawesson's reagent is added thereto, and the reaction is effected at a temperature within the range of room temperature to the reflux temperature of the solvent, thereby attaining the aimed object.

The material compounds (II), (II-a), (III), and (IV), which are used in the above-mentioned reaction formulas, are commercially available or can be easily synthesized by known methods. As examples of the known methods, the methods of reaction formulas F–K shown in FIGS. 6–11 can be listed. These methods are explained in the following.

Figure 7:
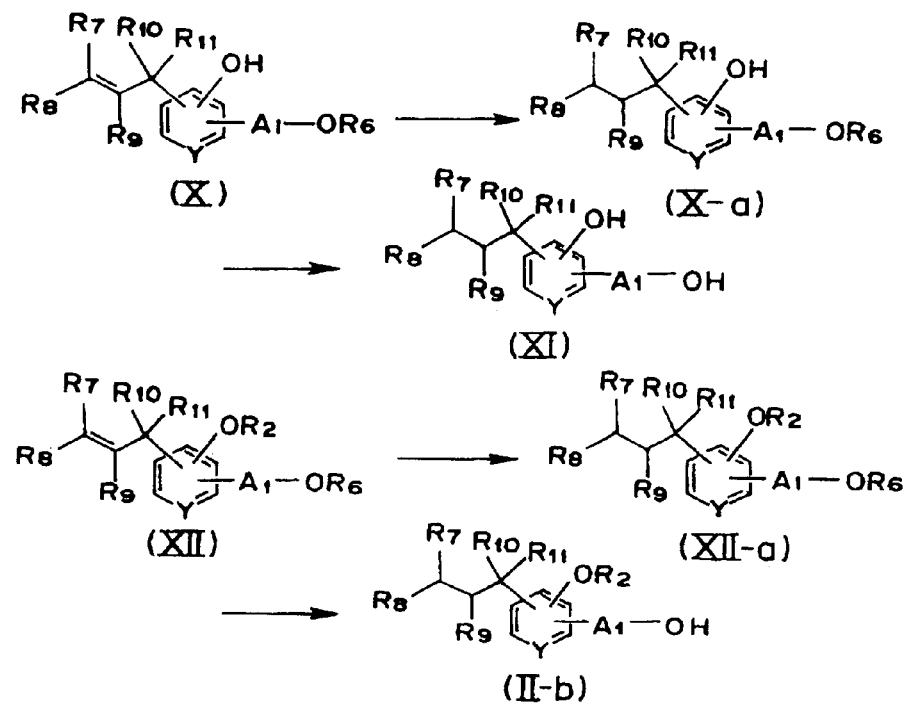

First, in the compound of formula (II), the compounds (II-b) and (XI) in which $R_1$ is a lower alkyl group, as shown in reaction formula G in FIG. 7, can be synthesized by the compounds (X) and (XII) having an alkenyl group correspond to $R_1$. The compounds (X) and (XII) can be synthesized by reaction formula F shown in FIG. 6.

In formulas F and G, $A_1$ represents —CO— or —CH$_2$CO—, while $R_7$, $R_8$, $R_9$, $R_{10}$, and $R_{11}$ represent a hydrocarbon atom or lower alkyl group. X represents a halogen atom. Also, $R_6$ represents a carboxyl protecting group and can use a lower alkyl group such as methyl, ethyl, isopropyl, t-butyl; phenacyl group; or trichloroethyl group, as long as no problem has occurred in the subsequent reaction. $R_2$ represents a lower alkyl, alkenyl, benzyl, or benzoyl group, while Y is defined as that in Formula (I).

In reaction formula F, the compound (X) can be obtained by alkenylation and Claisen rearrangement reaction with respect to the compound (VII). Further, the compound (XII) can be obtained by alkylation of the compound (X). Alkenylation reaction in formula F and alkylation reaction with respect to the compound (X) is effected by the same conditions with the reaction condition in reaction formula D.

Claisen rearrangement reaction in the second step of reaction formula F is conducted in the high boiling point solvent or without the presence of the solvent, under the ordinary pressure or application of pressure. As a solvent, for example, phenyl ether, N,N-dimethylaniline, or the like can be used. While the reaction temperature and reaction time may be changed according to the material compounds used, the reaction is usually effected at a temperature within the range between 100° C. and 200° C.

The compound (X) or (XII) obtained by formula F can be formed to the compounds (XI) and (II-b), by hydrogenation and deprotection of carboxyl protecting group as shown in reaction formula G. Hydrogenation at the first step in reaction formula G can use the known method. When the reaction is conducted under the catalytic reduction condition, for example, palladium, platinum, nickel, rhodium, ruthenium, or the like can be used as a catalyst. Specifically, for example, palladium-carbon is used under hydrogen gas atmosphere and the reaction is effected in the solvent such as ethanol ethyl acetate, tetrahydrofuran, or the like and at a temperature within the range of room temperature to the reflux temperature of the solvent, thereby attaining the aimed object.

Deprotection at the final step of reaction formula G can use the known ester hydrolysis method according to the types of protecting group $R_6$. For example, when $R_6$ is methyl or ethyl group, an inorganic base such as sodium hydroxide, or potassium hydroxide is used and the reaction is effected in the solvent such as water, ethanol containing water or methanol containing water and at a temperature within the range of room temperature to the reflux temperature of the solvent, thereby attaining the aimed object.

Figure 8:
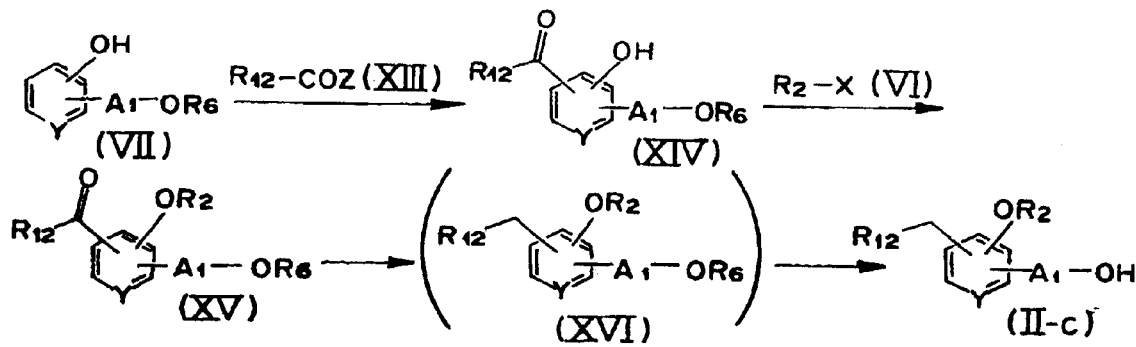

Also, the material compound (II-c) that $R_1$ is a lower alkyl group in formula (II) also can be synthesized by reaction formula H shown in FIG. 8.

In reaction formula H, $A_1$ represents —CO— or —CH$_2$CO—, while $R_{12}$ represents a lower alkyl group such as methyl, ethyl, isopropyl, or t-butyl group. X represents a halogen atom, while Z represents a chlorine atom or $R_{12}$COO-group. $R_6$ represents a carboxyl protecting group and can use a lower alkyl group such as methyl, ethyl, isopropyl, or t-butyl; phenacyl group; or trichloroethyl group, as long as no problem has occurred in the subsequent reaction. $R_2$ represents a lower alkyl, alkenyl, benzyl, or benzoyl group, while Y is defined as that in Formula (I).

In reaction formula H, the objective compound (II-c) can be obtained by conducting set of reaction of Friedel-Crafts acylation, alkylation of hydroxyl group, reduction of ketone, and deprotection with respect to the compound (VII). Friedel-Crafts acylation of the first step in the present reaction can be conducted by acting acid chloride or acid anhydride represented by formula (XIII) on the compound represented by formula (VII) in the presence of Lewis acid as a activating agent. As an activating agent, for example, Lewis acid such as aluminium chloride, antimony pentachloride, titanium tetrachloride, stannic tetrachloride, or boron trifluoride; trifluoroacetate anhydride; trimethylsilyl triflate; or the like can be used. As a solvent, for example, an aromatic compound such as nitrobenzene, a halogenated hydrocarbon such as dichloromethane, or 1,2-dichloroethane, carbon bisulfide, or the like can be used. While the reaction temperature and reaction time may be changed according to the material compounds used, the reaction is usually effected at a temperature within the range of −78° C. to the reflux temperature of the solvent. Specifically, for example, aluminium chloride is used as an activating agent and the reaction is effected in the solvent such as dichloromethane and at a temperature within the range of 0° C. to the room temperature, thereby attaining the aimed object.

Alkylation with respect to the compound (XIV) at the second step of reaction formula H can be conducted by the same condition with the reaction condition in reaction formula D.

In the reaction at the third step of reaction formula H, by reduction of the ketone in the compound (XV) the compound (XVI) or (II-c) can be obtained. The known methods can be used in the present reaction. For example, a condition such as Wolff-Kishner reduction, Clemmensen reduction, or the like can be used. In the case where Wolff-Kishner reduction is adopted, hydrazine and a strong base such as potassium hydroxide, sodium methoxide are used. The reaction is effected in high boiling point solvent such as diethylene glycol or without the solvent in the sealed tube at a temperature within the range between 150° C. and 200° C., thereby attaining the aimed object. In the case where Clemmensen reduction is adopted, diethylether, acetic anhydride, or the like is used as a solvent and the reaction is effected by reacting zinc or zinc amalgam in the presence of hydrochloric acid, thereby attaining the aimed object. Specifically, an inorganic base such as sodium hydroxide and hydrazine are used and the reaction is effected in the solvent such as ethylene glycol at a temperature within the range of 100° C. to the reflux temperature of the solvent, thereby attaining the aimed object. In the present reaction, the compound (II-c) may be obtained by deprotection of a carboxyl-protecting group $R_6$, depending on the condition. However, when the compound (XVI) is obtained, deprotection under the same reaction condition with the final step of reaction formula G, is conducted, thereby attaining the aimed object.

Figure 9:
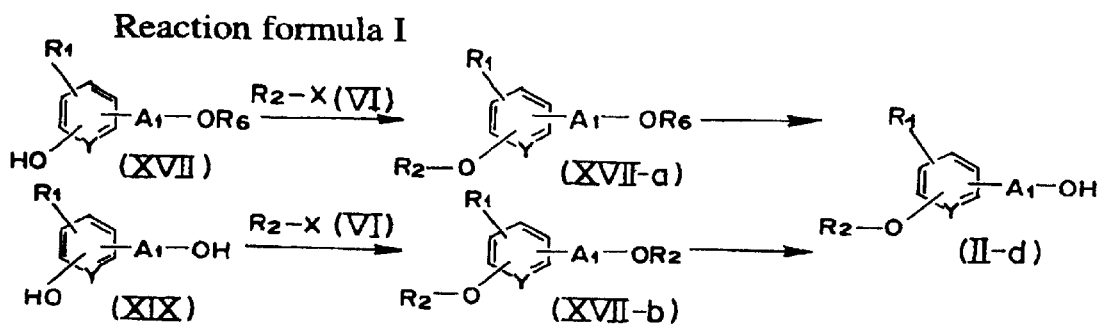

Also, as the examples of the other synthetic method of material compound (II), a method accompanying alkylation such as reaction formula I shown in FIG. 9 can be listed.

In reaction formula I, $A_1$ represents —CO— or —CH$_2$CO—, while X represents a halogen atom. $R_6$ represents a carboxyl protective group and can use a lower alkyl group such as methyl, ethyl, isopropyl, or t-butyl; phenacyl group; or trichloroethyl group, as long as no problem has occurred in the subsequent reaction. $R_2$ represents a lower alkyl, alkenyl, benzyl, or benzoyl group, while $R_1$ and Y are defined as those in Formula (I).

In reaction formula I, hydroxy compounds (XVII) and (XIX) are alkylated by hilide (VI) and hydrolyzed, thereby the compound (II-d) can be synthesized. Alkylation at the first step in the present reaction can be conducted under the same condition with the reaction condition of reaction formula D. Also, hydrolysis reaction of the second step in the present reaction can be conducted by the same condition with reaction formula G.

Figure 10:
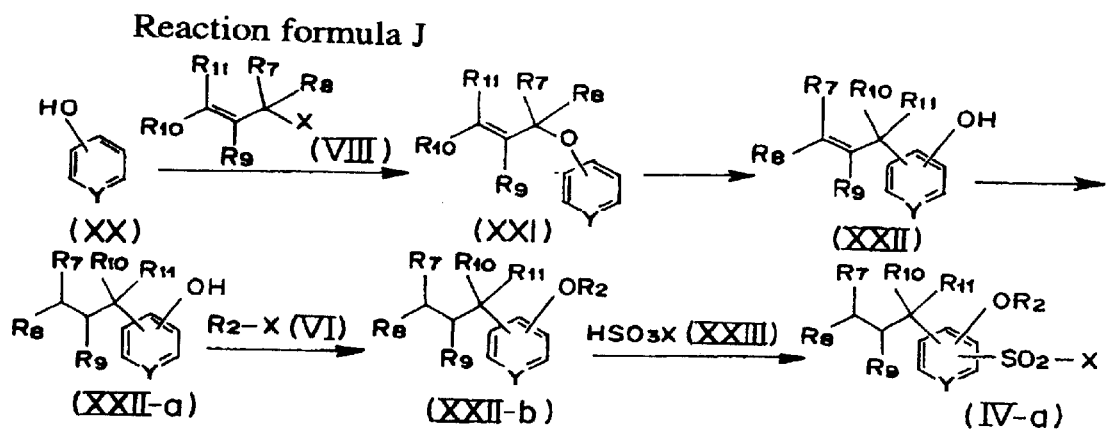

The material compound (IV) used in the above-mentioned reaction formula C can be synthesized by reaction formula J shown in FIG. 10. Also, in reaction formula J, $R_7$, $R_8$, $R_9$, $R_{10}$, and $R_{11}$ represent a hydrogen atom or lower alkyl group, while X represents a halogen atom. $R_2$ represents a lower alkyl, alkenyl, benzyl, or benzoyl group, while Y is defined as that in Formula (I).

In reaction formula J, the compound (IV-a) can be obtained by conducting set of reactions of alkenylation, Claisen rearrangement, hydrogenation, alkylation, and introduction of halogenated sulfonyl group to the compound (XX).

In formula J, alkenylation reaction of compound (XX), Claisen rearrangement of the compound (XXI), and alkylation reaction of the compound (XXII-a) can be conducted under the same condition with reaction formula F.

Hydrogenation with respect to the compound (XXII) at the third step in reaction formula J can be conducted under the same condition with reaction formula G.

In the reaction at the fifth step of formula J, the objective compound (IV-a) can be obtained by reacting a halogenated sulfuric acid such as chlorosulfuric acid on benzene ring of the compound expressed by formula (XXII-b). As a solvent, for example, carbon bisulfide, liquid sulfur dioxide, or a halogenated hydrocarbon such as dichloroethane, chloroform, dichloromethane, tetrachloroethane, or the like is used. While the reaction temperature and reaction time may be changed according to the material compounds used, the reaction is usually effected at a temperature within the range of 0° C. to the reflux temperature of the solvent.

Specifically, aromatic compound (XXII-b) is dissolved in chloroform, dichloroethane, or the like and the reaction is effected by reacting chlorosulfuric acid at a temperature within the range of 0° C. to the reflux temperature of the solvent, thereby attaining the aimed object.

Figure 11:
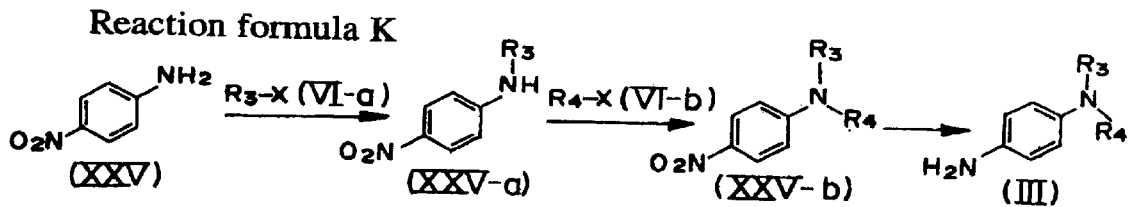

Next, the material compound (III) can be synthesized as like reaction formula K shown in FIG. 11. In reaction formula K, $R_3$ and $R_4$ are defined as those in formula (I).

In reaction formula K, the objective compound (III) can be obtained by successively alkylating the compound and by further reducing a nitro group.

Alkylation at the first and second steps of the present reaction can be conducted under the same condition with reaction formula D. Reduction of the nitro group of the compound (XXV-b) at the third step in the present reaction can use the known reactions. For example, a condition such as Birch reduction, Benkesser reduction, or the reduction using metal hydride complex compound, and the like can be used.

In the case where Birch reduction is adopted, metal such as lithium, sodium, or potassium is used and liquid ammonia is used as a solvent and then the reaction is conducted by coexisting methanol, ethanol, t-butanol, or the like as a proton source. While the reaction temperature and reaction time may be changed according to the material compounds used, the reaction is usually effected at a temperature within the range of −78° C. to the reflux temperature of the solvent. In the case where Benkesser reduction is adopted, for example, methylamine, ethylamine, or ethylenediamine is used as a solvent and the reaction is effected at a temperature within the range of −78° C. to the reflux temperature of the solvent, thereby attaining the aimed object. In the case where the reaction using metal hydride complex compound is adopted, sodium boron hydroxide is used. Water, methanol, ethanol, isopropanol, or the like is used as a solvent and then the reaction is conducted in the presence of 10% palladium/carbon, cyano nickel complex ion, or dichlorobis(triphenylphosphine) nickel (II) as a catalyst. While the reaction temperature and reaction time may be changed according to the material compounds used, the reaction is usually effected at a temperature within the range of 0° C. to the reflux temperature of the solvent.

Specifically, for example, dichlorobis(triphenylphosphine) nickel (II) of catalyst is dissolved in ethanol and, after sodium boron hydroxide and the compound (XXV-b) are added thereto, the reaction is effected at a temperature within the range of 0° C. to the reflux temperature of the solvent, thereby attaining the aimed object.

Here, in the material compounds used in the above mentioned reaction formulas, those not specified, for example, the compound (VI), (VII), (VIII), (XX), (XXV), or the like is commercially available or can be easily synthesized by known methods.

The compound expressed by formula (I) in accordance with the present invention can be changed to acid-added salts if necessary. Examples of the acid-added salts include salts in conjunction with inorganic acid such as hydrochloric acid, hydrobromic acid, sulfuric acid, or phosphoric acid and salts in conjunction with organic salts such as acetic acid, propionic acid, citric acid, lactic acid, oxalic acid, maleic acid, fumaric acid, succinic acid, tartaric acid, or methanesulfonic acid. These salts can be easily manufactured by normal methods.

When the phenylenediamine derivative in accordance with the present invention is used as a medicament for cerebral nerve diseases such as brain infarction and brain edema, it is generally used as a medicine for internal use or an injection.

When the compound of the present invention is used as a medicine for internal use, it may be administered orally as tablet, powder, granule, capsule, syrup, or the like as well as parenterally as suppository or the like. While the amount of administration may be outside of the range mentioned below according to the degree of symptom, personal difference, age, kind of symptom, or the like, it should of course be adjusted so as to fit the individual circumstances in specific cases. Usually 0.01 to 200 mg/kg or, preferably, 0.05 to 50 mg/kg or, more preferably, 0.1 to 10 mg/kg is administered per day for an adult in a single dose or several doses.

When formulating the medicament, a normal manufacturing method is used with a normal formulation carrier. If necessary, pharmacologically and pharmaceutically acceptable additives may be added thereto.

Namely, when preparing an oral solid formulation, after an excipient and, if necessary, a binder, a decaying agent, a luster, a coloring agent, a correctives, and the like are added to the main medicament, a normal method is used to form tablet, coated tablet, granule, powder, capsule, or the like.

Examples of the excipient include lactose, corn starch, sucrose, glucose, sorbitol, crystalline cellulose, and silicon dioxide. Examples of the binder include polyvinylalcohol, polyvinylether, ethyl cellulose, methyl cellulose, gum arabic, tragacanth, gelatin, shellac, hydroxypropyl cellulose, hydroxy propyl starch, and polyvinylpyrrolidone. Examples of the decaying agent include starch, agar, gelatin powder, crystalline cellulose, calcium carbonate, sodium hydrogencarbonate, calcium citrate, dextrin, and pectin. Examples of the luster include magnesium stearate, talc, polyethyleneglycol, silica, and hardened vegetable oil. As the coloring agent, those permitted to be added to medicines are used. Examples of the correctives include cocoa powder, menthol, aromatic acid, mentha oil, borneol, and cinnamon powder. If necessary, these tablet and granule can be coated with sugar-coating, gelatin-coating, and the like.

When the compound of the present invention is used as an injection, while the amount of administration may differ according to the degree of symptom, personal difference, age, or the like, usually 0.05 to 10 mg/kg or, preferably, 0.1 to 3 mg/kg is administered per day for an adult in a single dose or several doses.

The injection may be a sterile aqueous or non-aqueous solution, suspension, and emulsion. In such an injection, at least one active material is used as being mixed with at least one inactive aqueous diluent or inactive non-aqueous diluent. Further, if necessary, it may contain such adjuvants as antiseptic, wetting agent, emulsifier, dispersant, stabilizer, and dissolution adjuvant. In general, these are sterilized by filtration (e.g., by bacteria-blocking filter), compounding of sterilizer, or gamma-ray radiation or, after these treatments, turned into a solid composition by means of freeze-drying technique or the like and then sterile water or sterile injection diluent is added thereto immediately before use.

EXAMPLES

In the following, the embodiment of the present invention will be explained in further detail by using phenylenediamine derivatives in accordance with the present invention as examples.

Before the explanation of specific examples, the method for testing effects will be explained.

Radical Eliminating Effect Test (DPPH)

i) Meaning

Radical-eliminating ability of a sample drug is studied in terms of its reaction amount and reactivity with respect to $\alpha$, $\alpha$-diphenyl-$\beta$-picrylhydrazyl (DPPH) which is a stable radical.

ii) Method

Method of Uchiyama et al. (Japanese Journal of Pharmacology, vol. 88, pp. 678–683, 1968) was used. Namely, to a solution containing 20 mM acetic acid buffer (pH 5.5), 60% ethanol, and 10 $\mu$M of a sample compound, DPPH was added so as to yield a concentration of 0.1 mM. The resulting mixture was stirred and then its change in absorbance (ABS) at 517 nm was measured for 30 minutes at room temperature. Here, the sample compound was used as being dissolved in dimethylsulfoxide (DMSO). While the final concentration of DMSO was 10%, no influence upon the present system was observed.

iii) Judgment Standard

The DPPH reducing ratio of the sample compound at the concentration of 10 $\mu$M was calculated by the following equation:

reducing ratio (%)={1−(ABS after 30 minutes/initial ABS)}×100

Lipid Peroxidation Inhibition Test i) Meaning

In an automatic oxidation system using a rat brain homogenate, whether a sample compound having a radical-eliminating effect can actually have a lipid peroxidation inhibitory activity or not is investigated and its effectiveness is comparatively studied.

ii) Method

With reference to method of Shimamoto et. al. (Clinical Study of Free Radical, vol. 1, pp. 91–95, 1987), the following method was used. An SD-line male rat (7-week-old) was bled to death with a physiological saline perfusion under pentobarbital anesthesia. Then, its hemisphaerium cerebri was taken out and, while being cooled with ice, a 19-fold amount of 20 mM phosphoric acid buffer (pH 7.4) was added thereto. The resulting mixture was homogenized. To this mixture, 1 $\mu$M of the sample compound was added. After the resulting mixture was incubated for 1 hour at 37° C., the amount of generated lipid peroxide was determined by TBA method. Namely, to 0.2 ml of the homogenate, 0.2 ml of 8.1% SDS, 1.5 ml of 20% acetic acid buffer (pH 3.5), and 1.5 ml of 0.8% TBA reagent were added. The resulting mixture was incubated for 1 hour at 95° C. and then rapidly cooled with ice. Subsequently, 1 ml of distilled water and 5 ml of n-butanol/pyridine mixed solution (15:1, v/v) were added thereto and the mixture was stirred. After the mixture was centrifuged, the butanol layer was collected therefrom and its absorbance (a) at 535 nm was measured as compared with a blank. Also, as a reference liquid, a 10 $\mu$M solution of 1,1,3,3-tetraethoxypropane (TEP) was added in place of the brain homogenate and its absorbance (A) was measured in a similar manner. In the blank, a phosphoric acid buffer was used in place of the brain homogenate. The peroxide concentration was calculated by the following equation and defined as the brain lipid peroxide amount:

peroxide concentration (nmol/g wet weight)=a/A×100

The sample compound was used as being dissolved in dimethylsulfoxide (DMSO). While the final concentration of DMSO was 2%, no influence upon the present system was observed.

iii) Judgment Standard

The lipid peroxidation inhibitory rate of the sample compound at the concentration of 1 $\mu$M was calculated from the amount of increase in lipid peroxide in solvent-added group (M) and that in sample compound added group (m):

lipid peroxidation inhibitory rate (%)={1−(m/M)}×100

Brain Infarction Inhibition Test i) Meaning

The brain infarction inhibitory activity in vivo is studied. According to this test, it can be judged whether the peripherally administered sample compound can pass through the blood-brain barrier or not.

ii) Method

For the experiment, 9 to 10-week-old Crj:Fischer-344 line male rats were used. Each of all the soluble sample compounds was dissolved in a physiological saline and then administered intravenously or intraperitoneally. Each of insoluble ones was suspended in a physiological saline containing 0.1% Tween 80 and administered intraperitoneally. Also, those dissolved in a physiological saline containing 0.5% Tween 80 were used for intravenous administration. The intraperitoneal administration was effected 20 minutes before reperfusion, whereas the intravenous administration was effected simultaneously with reperfusion. As a control, only the base was administered. The surgical operation was effected in a manner similar to method of Koizumi et al. (Japanese Journal of Stroke, vol. 8, pp. 1–8, 1986) so as to form a middle cerebral artery (MCA) infarction model. Namely, the rat was subjected to inhalation anesthesia with 4% halothane and then, while the anesthesia was maintained with 1% halothane, fixed on face-up position. The neck portion was subjected to median incision such that the common carotid artery and outer carotid artery around the right carotid artery branching portion were separated from their surrounding connecting tissues and then ligated with a silk string. Further, the inner carotid artery starting portion was surrounded by a silk string so as to be ready for ligation and fixation which would be effected after insertion of an embolus. Then, the common carotid artery was incised and, from there, an embolus having a length of about 16 mm, in which a 4-0 surgical nylon string had been coated with a dental impression material, was inserted toward the inner carotid artery and its end near the nylon string was ligated and fixed to the inner carotid artery with the above mentioned silk string. Also, during the surgical operation, the body temperature was maintained by a small animal body temperature control apparatus in order to prevent it from lowering upon the whole anesthesia processes.

According to the foregoing operation, brain ischemia was effected for 2 hours and then the embolus was pulled out so as to effect reperfusion. The brain was taken out two hours after the reperfusion and then 4 pieces of crown-like separated strips were prepared by 2-mm intervals from the lambda level toward the downstream. These strips were immersed in 2% triphenyltetrazorium chloride (TTC) solution and incubated at 37° C., for 10 minutes. Thus dyed brain strips were immersed in a phosphate-buffered 8% formalin solution for 1 to 2 days and then photographed under a stereo-microscope (SZH10 ORINPAS). Thereafter, for each crown-like strip, the area of infarction region was measured by Planimeter (PLANIX 5000 TAMAYA).

iii) Judgment Standard

The effects of the sample compound were represented by its individual inhibitory rate (%) which used the total area of the infarction regions, which had not been dyed with TTC in the 4 strips.

The significance test was effected by student t-test.

individual inhibitory rate(%)={1−(value in sample group/value in control group)}×100

Brain Edema Inhibition Test i) Meaning

The brain edema inhibitory activity in vivo is confirmed. According to this test, it can be judged whether the peripherally administered sample compound can pass through the blood-brain barrier or not.

ii) Method

By using a 7 to 9-week-old Fischer rat (Charles River Japan Inc.), an MCA infarction reperfusion model was formed according to method of Koizumi et al. (Japanese Journal of Stroke, vol. 8, pp. 1–8, 1986). Namely, the rat was fixed face-up position under anesthesia with 2% halothane and then its neck portion was subjected to median incision so as to separate the right common carotid artery therefrom to the carotid artery branching portion while carefully keeping the vagus nerve. The outer carotid artery and inner carotid artery around the carotid artery branching portion were separated from their surrounding connecting tissues. Then, the common carotid artery and outer carotid artery were ligated with a silk string. Further, the inner carotid artery starting portion was surrounded by a silk string so as to be ready for ligation and fixation which would be effected after insertion of an embolus string. Then, the common carotid artery was incised and, from there, an embolus string was inserted toward the inner carotid artery by about 15 to 16 mm and then ligated and fixed to the inner carotid artery with the above mentioned silk string. As a result of the foregoing operation, the tip of the embolus string proceeded beyond the MCA branching portion so as to enter the anterior cerebral artery by about 1 to 2 mm and formed infarction at the MCA inlet by the body portion of the embolus string. After the embolus string blocking the MCA starting portion was left for a predetermined time, it was pulled out under halothane anesthesia to effect reperfusion. Here, in this model, since the right common carotid artery has been ligated, the blood flow is supposed to be restarted from the left inner carotid artery and vertebral-basilar by way of the anterior and posterior communicating arteries. This experiment effected two-hour ischemia and two-hour reperfusion.

Here, the embolus string was prepared in the following manner. Namely, a tip of a 4-0 surgical nylon string having a total length of 16 mm was held over an alcohol lamp so as to form a ball with a diameter of 0.2 to 0.3 mm and then a length of about 5 mm on the nearer side therefrom was coated with a dental impression material with reference to the size of the ball, thereby forming the embolus string.

The brain moisture content was measured by wet and dry weight method. Namely, after the head of the animal which had been subjected to ischemia or ischemic reperfusion was severed and its brain was taken out. After the resection of the cerebellum, the fore-brain was separated into right and left hemispheres which were immediately weighed respectively as ischemia side and non-ischemia side, thereby yielding their wet weight. Further, after being dried at 110° C. for 24 hours, their weight was measured again to yield dry weight. From thus obtained wet weight and dry weight, the brain moisture content was determined by the following equation:

brain moisture content (%)={((wet weight−dry weight)/wet weight}×100

The sample compound was suspended in a 0.05% Tween 80/physiological saline and 5 ml/kg of the suspension was intraperitoneally administered 20 minutes before reperfusion. Also, to a control, the base was administered alone in a similar manner.

iii) Judgment Standard

The results obtained were expressed by mean value± standard deviation. The significance test was effected by unpaired t-test or Welch's t-test and the difference was considered to be significant when the level of significance was less than 5% (P<0.05). The inhibitory rate was expressed by the following equation:

inhibitory rate(%)={(brain moisture content in control group−brain moisture content in sample group)/(brain moisture content in control group−brain moisture content in two-hour ischemia group)}×100

Compound Group 1

This group corresponds to the above-mentioned formula 2 wherein A is —CO— and $R_2$ is a hydrogen atom.

Example 1

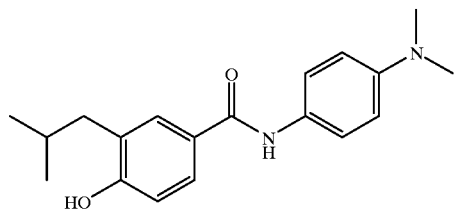

Example 2

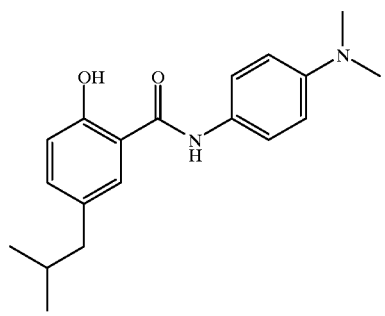

Example 3

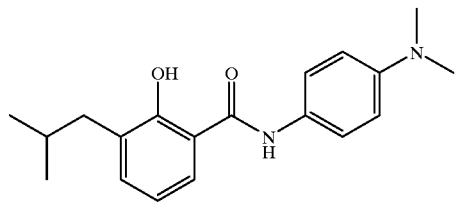

Example 4

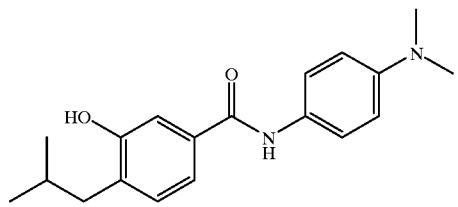

Example 5

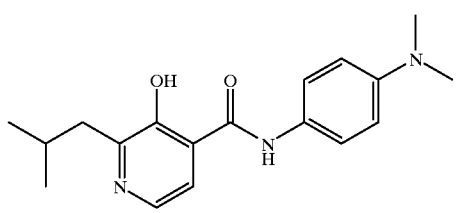

TABLE 1

| Sample compound | DPPH reducing ratio | Lipid peroxidation inhibitory ratio | Brain infarction[1] inhibitory ratio | Brain edema[2] inhibitory ratio |
|---|---|---|---|---|
| Example 1 | 22.9% | 40.1% | 53.0%* | 2.0% |
| Example 2 | 17.7 | 26.8 | 41.2 | |
| Example 3 | 22.5 | 22.7 | | |
| Example 4 | 16.4 | 13.5 | | |
| Example 5 | 16.1 | 29.5 | 19.0 | 38.1 |

*$p < 0.05$
[1] dose was 100 mg/kg
[2] dose was 100 mg/kg

As can be seen from the foregoing TABLE 1, the compounds belonging to this group 1 had a high DPPH reducing effect (radical-eliminating effect) as well as a lipid peroxidation inhibitory activity. Also, some compounds having brain infarction and brain edema inhibition activity were confirmed. The bonding position of $R_1$ and hydroxyl group had high degree of freedom and the carbon atom of Y may be nitrogen atom.

Compound Group 2

This group corresponds to the above mentioned formula 3 wherein A is —CO— and $R_2$ is a lower alkyl, alkenyl, benzyl or benzoyl group.

Example 6

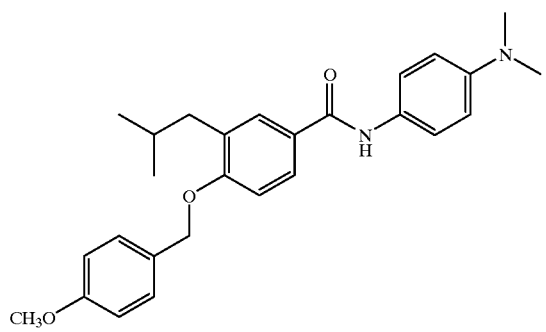

Example 7

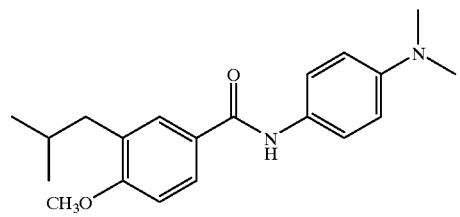

Example 8

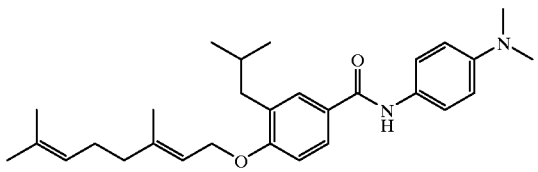

Example 9

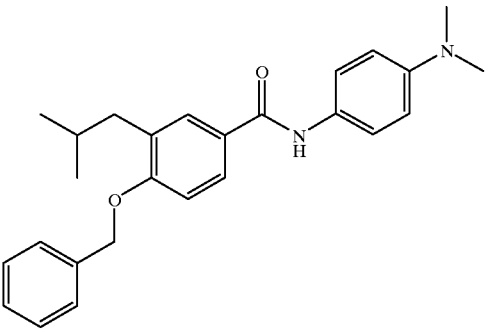

Example 10

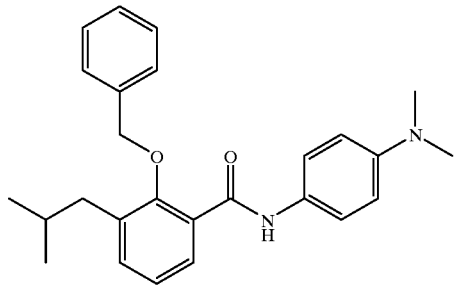

Example 11

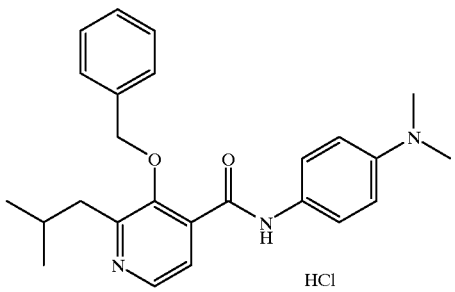

TABLE 2

| Sample compound | DPPH reducing ratio | Lipid peroxidation inhibitory ratio | Brain infarction[1] inhibitory ratio | Brain edema[2] inhibitory ratio |
|---|---|---|---|---|
| Example 6 | 25.1% | 41.7% | | 1.5% |
| Example 7 | 20.7 | 48.9 | | |
| Example 8 | 21.2 | 41.7 | | |
| Example 9 | 25.5 | 28.1 | 39.9% | 19.2 |
| Example 10 | 11.5 | 28.2 | 18.7 | |
| Example 11 | 9.6 | | | |

[1]dose was 100 mg/kg
[2]dose was 100 mg/kg

As can be seen from the foregoing TABLE 2, the compounds belonging to this group 2 had a high DPPH reducing effect (radical-eliminating effect) as well as a lipid peroxidation inhibitory activity. This tendency was widely recognized independent of the types of $R_2$. Also, some compounds having brain infarction and brain edema inhibition activity were confirmed. Further, the compounds such as Example 10, which was formed by converting the hydroxyl group of the Example 3 into benzyl group, showed brain infarction inhibition tendency.

Compound Group 3

This group corresponds to the above mentioned formula 4 wherein A is —$CH_2CO$—, —$SO_2$—, or —CS—.

Example 12

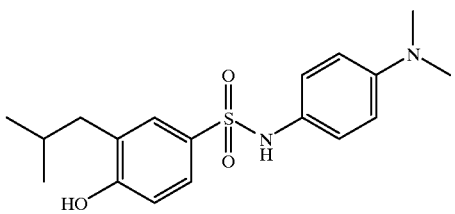

Example 13

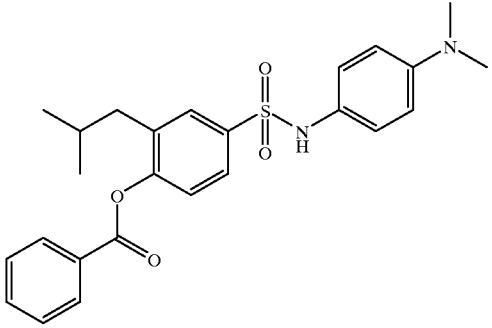

Example 14

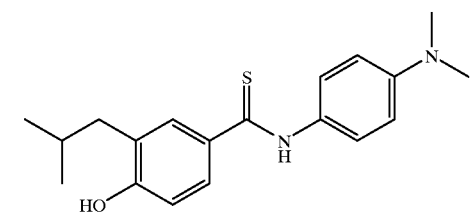

Example 15

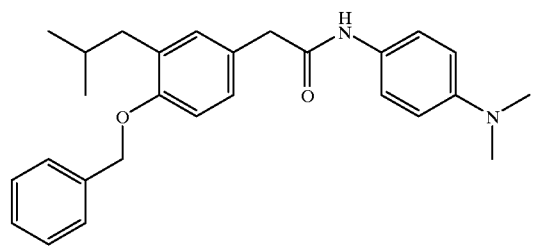

Example 16

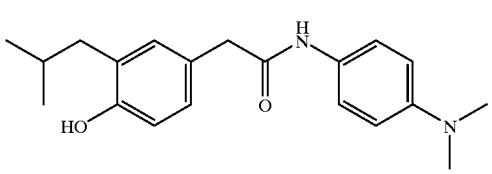

Example 17

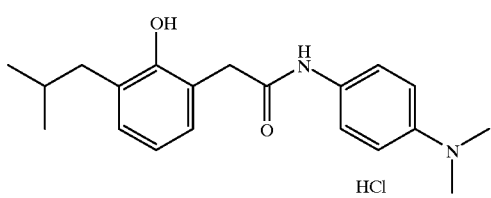

TABLE 3

| Sample compound | DPPH reducing ratio | Lipid peroxidation inhibitory ratio | Brain infarction[1] inhibitory ratio |
|---|---|---|---|
| Example 12 | 61.8% | 24.2% | 0.7% |
| Example 13 | 58.9 | 13.4 | |
| Example 14 | 18.3 | 33.9 | |
| Example 15 | 12.8 | 24.8 | 2.8 |
| Example 16 | 21.0 | 14.4 | |
| Example 17 | 18.7 | 10.4 | |

[1] dose was 100 mg/kg

As can be seen from the foregoing TABLE 3, the compounds belonging to this group 3 had a high DPPH reducing effect (radical-eliminating effect) as well as a lipid peroxidation inhibitory activity. Also, in this group A has a high degree of freedom in this group and may be —$CH_2CO$—, —$SO_2$—, or —$CS$—.

As explained in the above, the compound of the present invention has high DPPH reducing effect as well as a lipid peroxidation inhibitory activity. Also, the compound displays an excellent activity in brain infarction and brain edema inhibition. It is extremely rare compound that is useful for brain infarction and brain edema by one drug as a radical scavenger like this.

In the following, synthetic methods of the material compounds used for synthesizing Examples 1 to 17 will be shown as reference examples 1 to 7.

Reference Example 1
Synthesis of Ethyl 4-Hydroxy-3-isobutylbenzoate

Ethyl 4-hydroxybenzoate (50.0 g), methallyl chloride (32.6 g) and potassium carbonate (45.6 g) were refluxed with heating in acetone (150 ml) for 40 hours. The reaction mixture was filtrated and the filtrate was concentrated under a vacuum. The residue, after toluene (150 ml) was added thereto, was washed with 2% sodium hydroxide aqueous solution and water successively. The extract was dried over sodium sulfate anhydride and then concentrated under a vacuum, thereby yielding an oily compound. This compound was dissolved in N,N-dimethylaniline (80 ml) and refluxed with heating for about 10 hours. While being cooled with ice, the reaction mixture was acidified with concentrated hydrochloric acid and then extracted with toluene. The extract was extracted with 10% sodium hydroxide aqueous solution. The water layer was acidified with concentrated hydrochloric acid and then extracted with toluene. The extract was washed with water, dried over sodium sulfate anhydride and then concentrated under a vacuum, thereby yielding 59.2 g of ethyl 4-hydroxy-3-methallylbenzoate.

This compound (25.5 g) was dissolved in ethanol (250 ml) and then catalytic reduction was effected under a hydrogen gas atmosphere using 10%-palladium-carbon. After the reaction mixture was filtrated, the filtrate was concentrated under a vacuum, thereby yielding 25.6 g of the aimed compound as oil.

Reference Example 2
Synthesis of 4-Benzyloxy-3-isobutylbenzoic Acid

Ethyl 4-hydroxy-3-isobutylbenzoate (25.6 g), potassium carbonate (31.8 g), and benzyl bromide were refluxed with stirring in acetone (150 ml) for 4 hours. The reaction mixture, with water added thereto, was extracted with ethyl acetate. The extract was concentrated under a vacuum and the residue, after water (50 ml), potassium hydroxide (12.9 g), and ethanol (100 ml) were added thereto, was refluxed with heating for 2 hours. The reaction mixture, after water added thereto, was neutralized with hydrochloric acid and then extracted with ethyl acetate. The extract was washed with 10% hydrochloric acid aqueous solution and water, dried over magnesium sulfate anhydride and then concentrated under a vacuum. The resulting solid was recrystallized from n-hexane/ethanol, thereby yielding 29.0 g of the aimed compound.

Reference Example 3
Synthesis of Methyl 2-Hydroxy-5-isobutylylbenzoate

Into a solution of aluminum chloride anhydride (236.1 g) in dichloromethane (400 ml) was dropped methyl salicylate (98.0 g) while being cooled with ice. Isobutylyl chloride (125.8 g) was dropped thereto for 2 hours while keeping the temperature of the reaction system at less than 15° C. and then stirred for 12 hours. The reaction mixture was dropped into water with ice and the organic phase was washed with water, saturated sodium hydrogencarbonate aqueous solution, and water successively, dried over magnesium sulfate anhydride, and then concentrated under a vacuum, thereby yielding 143.0 g of the aimed compound.

Reference Example 4
Synthesis of Methyl 2-Benzyloxy-5-isobutylylbenzoate

In a manner similar to Reference Example 2, methyl 2-hydroxy-5-isobutylylbenzoate (117.0 g) was subjected to alkylation using benzyl chloride (66.7 g), thereby yielding 161.1 g of the aimed compound.

Reference Example 5
Synthesis of 2-Benzyloxy-5-isobutylbenzoic Acid

Methyl 2-benzyloxy-5-isobutylylbenzoate(161.1 g), sodium hydroxide(130.4 g), hydrazine monohydrate (103.3 g) were dissolved in ethylene glycol (1400 ml) and the mixture was stirred at 15° C. for 5 hours. The reaction mixture, with water added thereto, was acidified with 3N hydrochloric acid and then extracted with dichloromethane. The organic layer was washed with water, dried over magnesium sulfate anhydrite, and then concentrated under a vacuum. The residue was purified by silica gel column chromatography (chloroform) and then the resulting solid was recrystallized from dichloromethane/n-hexane, thereby yielding 48.6 g of the aimed compound.

Reference Example 6
Synthesis of 2-Benzyloxy-3-isobutylbenzoic Acid

In a manner similar to Reference Example 1 and 2, methyl salicylate was subjected to methallylation, Claisen rearrangement to 3-position, catalytic hydrogenation, benzylation, hydrolysis with base successively, thereby yielding the aimed compound.

Reference Example 7
Synthesis of 3-Benzyloxy-4-isobutylbenzoic Acid

In a manner similar to Reference Example 1 and 2, ethyl 3-hydroxybenzoate (298 g) was subjected to methallylation, Claisen rearrangement to 4-position, catalytic hydrogenation, benzylation, hydrolysis with base successively, thereby yielding 31.7 of the aimed compound.

Example 1

The compound of Example 9 (2.00 g) was dissolved in ethanol (70 ml) and then 10%-palladium-charcoal was added thereto. The mixture was subjected to the debenzylation under hydrogen gas atmosphere while being stirred at room temperature for 48 hours. The reaction mixture was filtrated under a vacuum and the filtrate was concentrated under a vacuum. The resulting solid was recrystallized from n-hexane/ethyl acetate, thereby yielding 1.45 g of the aimed compound.

mp 189.0–190.2° C.

$^1$H-NMR(DMSO-d$_6$)δ 0.88(6H, d, J=6.4 Hz), 1.93(1H, m), 2.45(2H, d, J=8.3 Hz), 2.86(6H, s), 6.70(2H, d, J=7.3 Hz), 6.84(1H, d, J=7.8 Hz), 7.53(2H, d, J=8.3 Hz), 7.66(1H, d, J=7.8 Hz), 7.67(1H, s), 9.66(1H, s), 9.84(1H, br.s)

Example 2

In a manner similar to Example 9, 2-benzyloxy-5-isobutylbenzoic acid (4.18 g) was condensed with N,N-dimethyl-1,4-phenylenediamine (2.00 g), thereby yielding 5.34 g of the protected compound in which a hydroxyl group of the aimed compound was protected with benzyl group.

In a manner similar to Example 1, this protected compound was subjected to catalytic reduction, thereby yielding 1.31 g of the aimed compound.

mp 156.7–157.0° C.

1H-NMR(DMSO-d$_6$) δ 0.87(6H, d, J=6.3 Hz), 1.92(1H, m), 2.45(2H, d, J=6.8 Hz), 2.86(6H, s), 6.71(2H, d, J=7.3 Hz), 7.11(1H, d, J=7.3 Hz), 7.30(1H, d, J=7.3 Hz), 7.32(1H, s), 7.55(2H, d, J=7.3 Hz), 9.52(1H, s), 9.83(1H, s)

Example 3

In a manner similar to Example 1, the compound of Example 10 (2.14 g) was subjected to catalytic reduction, thereby yielding 1.23 g of the aimed compound.

mp 106.0° C.

$^1$H-NMR(DMSO-d$_6$)δ 0.87(6H, d, J=6.8 Hz), 1.94(1H, m), 2.47(2H, d, J=7.3 Hz), 2.89(6H, s), 6.74(2H, d, J=8.8 Hz), 6.85(1H, dd, J=7.3, 7.8 Hz), 7.28(1H, d, J=7.3 Hz), 7.46(2H, d, J=8.8 Hz), 7.90(1H, d, J=7.8 Hz), 10.22(1H, S), 12.95(1H, S)

Example 4

In a manner similar to Example 9, 3-benzyloxy-4-isobutylbenzoic acid (3.14 g) was condensed with N,N-dimethyl-1,4-phenylenediamine (1.50 g), thereby yielding 3.68 g of the protected compound in which a hydroxyl group of the aimed compound was protected with benzyl group.

In a manner similar to Example 1, this protected compound was subjected to catalytic reduction, thereby yielding 1.29 g of the aimed compound.

mp 143.1–144.1° C.

$^1$H-NMR(DMSO-d$_6$)δ 0.87(6H, d, J=6.8 Hz), 1.85(1H, m), 2.42(2H, d, J=6.8 Hz), 2.89(6H, s), 6.74(2H, d, J=8.8 Hz), 6.86(1H, d, J=8.3 Hz), 7.21(1H, d, J=8.3 Hz), 7.47(2H, d, J=8.8 Hz), 7.80(1H, s), 10.16(1H, s), 12.05(1H, br.s)

Example 5

In a manner similar to Example 1, the free compound of Example 11 (2.12 g) was subjected to catalytic reduction, thereby yielding 1.56 g of the aimed compound.

mp 151.0–152.7° C.

$^1$H-NMR (DMSO-d$_6$)δ 0.90(6H, d, J=4.3 Hz), 2.17(1H, m), 2,72(2H, d, J=7.3 Hz), 2.93(6H, s), 7.58(3H, m), 7.83 (1H, m), 7.89(2H, m).

Example 6

The compound of Example 1 (0.78 g), methoxybenzyl chloride (0.47 g), and potassium carbonate (1.38 g) were refluxed with stirring in acetone (60 ml) for 22 hours. The reaction mixture was filtrated and the filtrate was concentrated under a vacuum. The residue was extracted with ethyl acetate. The organic layer was washed with water and saturated brine, dried over sodium sulfate anhydride and then concentrated under a vacuum. The resulting solid was recrystallized from n-hexane/acetone, thereby yielding 0.94 g of the aimed compound.

mp 182.0–182.7° C.

$^1$H-NMR (CDCl$_3$)δ 0.91(6H, d, J=6.8 Hz), 1.98(1H, m), 2.57(2H, d, J=6.8 Hz), 2.9(6H, s), 3.83(3H, s), 5.06(2H, s), 6.75(2H, d, J=8.8 Hz), 6.92–6.96(3H, m), 7.35(2H, d, J=8.8 Hz), 7.47(2H, d, J=8.8 Hz), 7.55(1H, s), 7.65(1H, s), 7.66–7.68(1H, m).

Example 7

In a manner similar to Reference Example 2 and Example 1, 4-benzyloxy- 3-isobutylbenzoic acid (3.07 g) was subjected to catalytic reduction, methylation, and hydrolysis successively, thereby yielding 1.69 g of 3-isobutyl-4-methoxybenzoic acid.

After this compound was dissolved in anhydrous tetrahydrofuran (17 ml), N,N'-carbonyldiimidazole (0.73 g) was added thereto while being cooled with ice. After being stirred at room temperature for 30 minutes, the reaction mixture, with N,N-dimethyl-1,4-phenylenediamine (0.55 g) added thereto, was stirred at room temperature for 22 hours. The reaction mixture was added to water and then extracted with ethyl acetate. The organic layer was washed with saturated brine, dried over sodium sulfate anhydride and then concentrated under a vacuum. The residue was purified by silica gel column chromatography (chloroform:methanol=10:1), thereby yielding 0.85 g of the aimed compound.

mp 156.7–157.0° C.

$^1$H-NMR (CDCl$_3$)δ 0.90(6H, d, J=6.8 Hz), 1.80–2.00(1H, m), 2.53(2H, d, J=7.3 Hz), 2.93(6H, s), 3.86(3H, s), 6.74 (2H, d, J=8.8 Hz), 6.88(1H, d, J=8.3 Hz), 7.4(2H, d, J=8.8 Hz), 7.59(1H, s), 7.61(1H, d, J=2.0 Hz), 7.70(1H, dd, J=2.0, 8.3 Hz).

Example 8

In a manner similar to Reference Example 2, the compound of Example 1 (0.70 g) was subjected to geranylation using geranyl bromide (0.60 g), thereby yielding 0.77 g of the aimed compound.

mp 81.2–82.0° C.

$^1$H-NMR (DMSO-d$_6$)δ 0.87(6H, d, J=6.8 Hz), 1.57(3H, s), 1.63(3H, s), 1.72(3H, s), 1.90–1.98(1H, m), 2.04–2.10 (4H, m), 2.87(6H, s), 4.62(2H, d, J=6.8 Hz), 5.08(1H, m), 5.43(1H, m), 6.72(2H, d, J=8.8 Hz), 7.04(1H, d, J=8.8 Hz), 7.54(2H, d, J=8.8 Hz), 7.72(1H, s,), 7.81(1H, d, J=8.8 Hz), 9.74(1H, s).

Example 9

4-benzyloxy-3-isobutylbenzoic acid (3.14 g) was dissolved in the mixture of dichloromethane (45 ml) and triethylamine (3.08 ml) and then diphenylphosphinic chloride (2.66 g) was added thereto while being cooled with ice. After being stirred for 90 minutes, the reaction mixture, with N,N-dimethyl-1,4-phenylenediamine (1.50 g) added thereto, was stirred at room temperature for 15 hours. The reaction mixture was washed with saturated sodium hydrogencarbonate aqueous solution and saturated brine, dried over sodium sulfate anhydride and then concentrated under a vacuum. The resulting solid was recrystallized from n-hexane/chloroform, thereby yielding 3.27 g of the aimed compound.

mp 165.7–167.2° C.

$^1$H-NMR(DMSO-d$_5$)δ 0.88(6H, d, J=6.8 Hz), 1.96(1H, m), 2.52(2H, d, J=6.8 Hz), 2.87(6H, s), 5.21(2H, s), 6.72 (2H, d, J=8.3 Hz), 7.34~7.48(5H, m), 7.54(2H, d, J=8.3 Hz), 7.75(1H, s), 7.81(1H, br.d, J=8.3 Hz), 9.78(1H, s)

Example 10

In a manner similar to Example 9, 2-benzyloxy-3-isobutylbenzoic acid (3.14 g) was condensed with N,N-dimethyl-1,4-phenylenediamine (1.50 g), thereby yielding 4.44 g of the aimed compound.

$^1$H-NMR(DMSO-d$_6$)δ 0.87(6H, d, J=6.4 Hz), 1.94(1H, m), 2.50(2H, m), 2.86(6H, s), 4.92(2H, s), 6.70(2H, d, J=8.8 Hz), 7.16~7.40(8H, m), 7.51(2H, d, J=8.8 Hz), 10.02(1H, s)

Example 11

In a manner similar to Example 9, 2-benzyloxy-3-isobutylisonicotinic acid (2.00 g) was condensed with N,N-dimethyl-1,4-phenylenediamine (1.19 g), thereby yielding 2.97 g of the acid-free compound of the aimed compound.

This acid-free compound was dissolved in diethyl ether and then 1N-hydrochloric acid ether solution (15 ml) was added thereto. After being stirred at room temperature for 10 minutes, the depositing crystals were collected by filtration, thereby yielding 3.24 g of the aimed compound.

$^1$H-NMR(DMSO-d$_6$)δ 0.88(6H, d, J=6.0 Hz), 2.10–2.30 (1H, m), 2.80–2.90(2H, m), 3.09(6H, s), 5.10(2H, s), 7.33–7.36(4H, m), 7.74–7.84(4H, m), 8.59(1H, m), 11.05–11.33(1H, m)

Example 12

The solution of the compound of Example 13 (1.00 g) and sodium hydroxide (0.16 g) dissolved in the mixture of methanol (40 ml) and tetrahydrofuran (5 ml) was stirred for 2 hours while being cooled with ice. The reaction mixture was neutralized with ammonium chloride and then extracted with ethyl acetate. The organic layer was washed with saturated sodium hydrogencarbonate and saturated brine, dried over sodium sulfate anhydride and then concentrated under a vacuum. The residue was purified by silica gel column chromatography (n-hexane:ethyl acetate=2:1), thereby yielding 0.76 g of the aimed compound.

mp 120.5–122.2° C.

$^1$H-NMR (DMSO-d$_6$)δ 0.76(6H, d, J=6.8 Hz), 1.73–1.79 (1H, m), 2.34(2H, d, J=7.3 Hz), 2.79(6H, s), 6.54(2H, d, J=8.8 Hz), 6.80–6.83(3H, m), 7.24(1H, d, J=2.5 Hz), 7.31 (1H, dd, J=2.5, 8.3 Hz), 9.29(1H, brs), 10.18(1H, brs).

Example 13

In a manner similar to Reference Example 1, phenol (100 g) was subjected to methallylation, Claisen rearrangement, and catalytic hydrogenation successively, thereby yielding 42.0 g of 2-isobutylphenol.

To the solution of this compound (42.0 g) in pyridine (210 ml) was added benzoyl chloride (41.3 g). After being stirred at room temperature for 12 hours, the reaction mixture, with water added thereto, was extracted with chloroform. The organic layer was washed with water and saturated brine, dried over magnesium sulfate anhydride and then concentrated under a vacuum. The residue was purified by silica gel column chromatography (n-hexane), thereby yielding 45.0 g of o-(benzoyloxy)isobutylbenzene.

To the solution of this compound (20.0 g) in chloroform (100 ml) was added sulfonyl chloride (20.2 g). After being stirred at 60° C. for 1 hour, the reaction mixture, with water added thereto, was extracted with chloroform. The organic layer was washed with water and saturated brine, dried over magnesium sulfate anhydride and then concentrated under a vacuum. The residue was purified by silica gel column chromatography (n-hexane:chloroform=1:1), thereby yielding 4.1 g of 4-benzoyloxy-3-isobutylbenzenesulfonyl chloride.

This compound (2.00 g) was dissolved in the mixture of tetrahydrofuran (50 ml) and triethylamine (3.0 ml) and then N,N-dimethyl-1,4-phenylenediamine (0.76 g) was added thereto. After being stirred at room temperature for 24 hours, the reaction mixture was washed with saturated sodium hydrogencarbonate aqueous solution and saturated brine, dried over sodium sulfate anhydride and then concentrated under a vacuum. The resulting solid was recrystallized from n-hexane/chloroform, thereby yielding 2.22 g of the aimed compound.

mp 134.0–138.5° C.

$^1$H-NMR (CDCl$_3$)δ 0.80(6H, d, J=6.7 Hz), 1.76–1.79(1H, m), 2.44(2H, d, J=6.8 Hz), 2.91(6H, s), 6.06(1H, s), 6.57 (2H, d, J=9.3 Hz), 6.91(2H, d, J=9.3 Hz), 7.52–7.70(5H, m), 8.17(1H, s), 8.19(1H, s).

Example 14

To the solution of the compound of Example 9 (0.61 g) in toluene (30 ml) was added lawesson's reagent (0.30 g). After being refluxed with stirring for 3 hours, the reaction mixture, with saturated brine added thereto, was extracted with ethyl acetate. The organic layer was washed with saturated sodium hydrogencarbonate and brine, dried over sodium sulfate anhydride and then concentrated under a vacuum. In a manner similar to Example 1, the residue was subjected to catalytic reduction, thereby yielding 0.28 g of the aimed compound.

mp 219.0–221.5° C.

$^1$H-NMR (CDCl$_3$)δ 0.96(6H, d, J=7.0 Hz), 1.95–2.05(1H, m), 2.53(2H, d, J=7.3 Hz), 2.99(6H, s), 4.95(1H, s), 6.73–6.81(3H, m), 7.54(2H, d, J=8.8 Hz), 7.65–7.69(2H, m), 8.82(1H, s).

Example 15

In a manner similar to Reference Example 1 and 2, 4-hydroxyphenylacetic acid (150.0 g) was subjected to methallylation, rearrangement, catalytic hydrogenation, benzylation, and hydrolysis successively, thereby yielding 70.4 g of 4-benzyloxy-3-isobutylphenylacetic acid.

In a manner similar to Example 9, this compound (2.00 g) was condensed with N,N-dimethyl-1,4-phenylenediamine (1.31 g), thereby yielding 2.01 g of the aimed compound.

mp 109.5–110.0° C.

$^1$H-NMR (DMSO-d$_6$)δ 0.86(6H, d, J=6.8 Hz), 1.85–1.93 (1H, m), 2.46(2H, d, J=6.8 Hz), 2.83(6H, s), 3.46(2H, s), 5.08(2H, s), 6.66(2H, d, J=8.8 Hz), 6.96(1H, d, J=8.3 Hz), 7.07– 7.08(2H, m), 7.36–7.44(7H, m), 9.75(1H, s).

Example 16

In a manner similar to Example 1, the compound of Example 15 (1.17 g) was subjected to debenzylation, thereby yielding 0.81 g of the aimed compound.

mp 50.0–51.0° C.

¹H-NMR (DMSO-d₆)δ 0.85(6H, d, J=6.8 Hz), 1.83–1.87 (1H, m), 2.36(2H, d, J=7.3 Hz), 2.87(6H, s), 3.40(2H, s), 6.65–6.71(3H, m), 6.91–6.96(2H, m), 7.37(2H, d, J=9.3 Hz), 9.03(1H, s), 9.71(1H, s).

Example 17

(2-benzyloxy-3-isobutylphenyl)acetic acid was obtained by using a manner similar to the synthesis method for 2-bezyloxy-3-isobutylbenzoic acid in Reference Example 6.

(2-benzyloxy-3-isobutylphenyl)acetic acid (10.00 g) was refluxed in mixture of glacial acetic acid (25 ml) and concentrated hydrochloric acid (15 ml). The reaction mixture, with saturated sodium hydrogencarbonate aqueous solution, was extracted with ethyl acetate. The organic layer was washed with saturated sodium hydrogencarbonate aqueous solution and brine, dried over sodium sulfate anhydride and then concentrated under a vacuum. In a manner similar to Example 9 and 11, the residue was subjected to condensation with N,N-dimethyl-1,4-phenylenediamine (1.31 g) and then to reaction forming salt with hydrochloric acid, thereby yielding 0.44 g of the aimed compound.

mp 166.5–168.5° C.

¹H-NMR(CDCl₃)δppm 0.92(6H, d, J=6.8 Hz), 1.90–2.05 (1H, m), 2.54(2H, d, J=6.8 Hz), 3.14(6H, s), 3.88(2H, s), 6.78(1H, t, J=7.5 Hz), 7.01(1H, d, J=7.8 Hz), 7.17(1H, d, J=5.9 Hz), 7.58(2H, d, J=8.8 Hz), 7.83(2H, d, J=9.3 Hz), 8.65(1H, s), 9.65(1H, s)

What is claimed is:

1. A phenylenediamine derivative or a pharmacologically acceptable salt thereof expressed by the following formula 1:

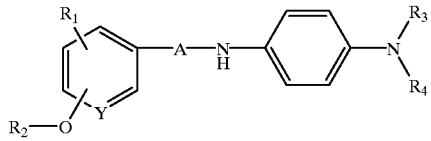

wherein A represents a group expressed by —CO—, —CH₂CO—, —CS—, or —SO₂—; Y represents a carbon atom; R₁ represents a lower alkyl group; R₂ represents a hydrogen atom, or a lower alkyl, benzyl, or benzoyl group; and each of R₃ and R₄ represents an alkyl group having 1–10 carbon atoms.

2. A phenylenediamine derivative or a pharmacologically acceptable salt thereof according to claim 1, wherein A is a group expressed by —CO—.

3. A phenylenediamine derivative or a pharmacologically acceptable salt thereof according to claim 1, wherein R₃ and R₄ are methyl group.

4. A phenylenediamine derivative or a pharmacologically acceptable salt thereof according to claim 1, wherein R₁ is isobutyl group.

5. A phenylenediamine derivative or a pharmacologically acceptable salt thereof according to claim 1, as expressed by the following formula 2:

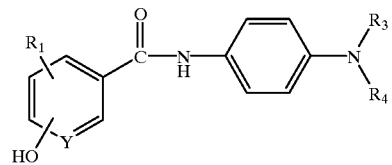

wherein Y represents a carbon atom; R₁ represents a lower alkyl group; and each of R₃ and R₄ represents an alkyl group having 1–10 carbon atoms.

6. A phenylenediamine derivative or a pharmacologically acceptable salt thereof according to claim 5, wherein R₃ and R₄ are methyl group.

7. A phenylenediamine derivative or a pharmacologically acceptable salt thereof according to claim 5, wherein R₁ is isobutyl group.

8. A phenylenediamine derivative or a pharmacologically acceptable salt thereof according to claim 1, as expressed by the following formula 3:

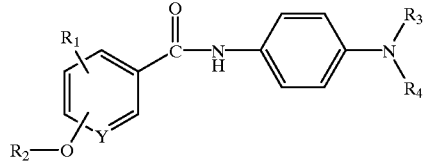

wherein Y represents a carbon atom; R₁ represents a lower alkyl group; R₂ represents a lower alkyl, benzyl, or benzoyl group; and each of R₃ and R₄ represents an alkyl group having 1–10 carbon atoms.

9. A phenylenediamine derivative or a pharmacologically acceptable salt thereof according to claim 8, wherein R₃ and R₄ are methyl group.

10. A phenylenediamine derivative or a pharmacologically acceptable salt thereof according to claim 8, wherein R₁ is isobutyl group.

11. A phenylenediamine derivative or a pharmacologically acceptable salt thereof according to claim 1, as expressed by the following formula 4:

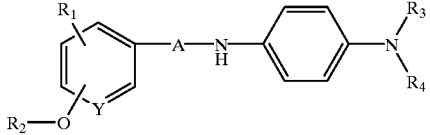

wherein Y represents a carbon atom; A represents a group expressed by —CH₂CO—, —CS—, or —SO₂; R₁ represents a lower alkyl group; R₂ represents a hydrogen, a lower alkyl, benzyl, or benzoyl group; and each of R₃ and R₄ represents an alkyl group having 1–10 carbon atoms.

12. A phenylenediamine derivative or a pharmacologically acceptable salt thereof according to claim 11, wherein R₃ and R₄ are methyl group.

13. A phenylenediamine derivative or a pharmacologically acceptable salt thereof according to claim 11, wherein R₁ is isobutyl group.

14. A radical scavenger composition comprising, as an effective ingredient, a phenylenediamine derivative or a pharmacologically acceptable salt thereof according to claim 1, together with a pharmaceutically acceptable carrier and/or adjuvant.

15. A brain infarction depressant composition comprising, as an effective ingredient, a phenylenediamine derivative or a pharmacologically acceptable salt thereof according to claim 1, together with a pharmaceutically acceptable carrier and/or adjuvant.

16. A brain edema depressant composition comprising, as an effective ingredient, a phenylenediamine derivative or a pharmacologically acceptable salt thereof according to claim 1, together with a pharmaceutically acceptable carrier and/or adjuvant.

17. A method for inhibiting a brain infarction in man or mammals, which comprises administering an effective amount of a phenylenediamine derivative or a pharmacologically acceptable salt thereof according to claim 1 to a host in need of said treatment.

18. A method for inhibiting a brain edema in man or mammals, which comprises administering an effective amount of a phenylenediamine derivative or a pharmacologically acceptable salt thereof according to claim 1 to a host in need of said treatment.

* * * * *